US012566174B2

(12) United States Patent
Pentyala et al.

(10) Patent No.: US 12,566,174 B2
(45) Date of Patent: Mar. 3, 2026

(54) METHOD AND KIT FOR DETERMINING THE PRESENCE OF MONOSODIUM URATE CRYSTALS IN JOINT SYNOVIAL FLUID

(71) Applicant: THE RESEARCH FOUNDATION FOR THE STATE UNIVERSITY OF NEW YORK, Albany, NY (US)

(72) Inventors: Srinivas Pentyala, Albany, NY (US); Lawrence Hurst, Albany, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 542 days.

(21) Appl. No.: 16/609,587

(22) PCT Filed: May 11, 2018

(86) PCT No.: PCT/US2018/032220
§ 371 (c)(1),
(2) Date: Oct. 30, 2019

(87) PCT Pub. No.: WO2018/209178
PCT Pub. Date: Nov. 15, 2018

(65) Prior Publication Data
US 2020/0150111 A1     May 14, 2020

Related U.S. Application Data

(60) Provisional application No. 62/504,623, filed on May 11, 2017.

(51) Int. Cl.
| | |
|---|---|
| *G01N 33/53* | (2006.01) |
| *B01L 3/00* | (2006.01) |
| *G01N 1/30* | (2006.01) |

(52) U.S. Cl.
CPC ........ *G01N 33/5308* (2013.01); *B01L 3/5085* (2013.01); *G01N 1/30* (2013.01); *B01L 2300/043* (2013.01); *B01L 2300/0654* (2013.01); *G01N 2001/302* (2013.01); *G01N 2800/107* (2013.01)

(58) Field of Classification Search
CPC ................. G01N 1/30; G01N 33/5308; G01N 2800/107; B01L 3/5085
See application file for complete search history.

(56) References Cited

U.S. PATENT DOCUMENTS

| | | | |
|---|---|---|---|
| 4,212,844 A | 7/1980 | Werner et al. | |
| 4,416,998 A | 11/1983 | Adams et al. | |
| 4,434,234 A | 2/1984 | Adams et al. | |
| 4,552,848 A | 11/1985 | Yudelson et al. | |
| 4,575,452 A | 3/1986 | Lee et al. | |
| 4,687,736 A | 8/1987 | Newman et al. | |
| 4,772,487 A * | 9/1988 | Gotoh ................. | G01N 35/028 |
| | | | 118/712 |

| | | |
|---|---|---|
| 5,064,768 A | 11/1991 | Ebata et al. |
| 5,116,734 A | 5/1992 | Higgs et al. |
| 5,567,585 A | 10/1996 | Caetano-Anolles et al. |
| 5,637,508 A | 6/1997 | Kidwell et al. |
| 6,130,023 A | 10/2000 | Coppens et al. |
| 6,426,195 B1 | 7/2002 | Zhong et al. |
| 6,455,064 B1 | 9/2002 | Narang et al. |
| 6,602,669 B2 | 8/2003 | Letsinger et al. |
| 6,654,120 B2 | 11/2003 | Ban |
| 6,699,720 B1 | 3/2004 | McMillan |
| 7,144,738 B2 | 12/2006 | Whitney |
| 7,147,996 B2 | 12/2006 | Fitterman et al. |
| 7,183,072 B1 | 2/2007 | Hainfeld |
| 7,592,153 B2 | 9/2009 | Hainfeld |
| 7,632,652 B2 | 12/2009 | Bieniarz et al. |
| 7,888,060 B2 | 2/2011 | Hainfeld et al. |
| 7,951,554 B2 | 5/2011 | Hainfeld et al. |
| 8,153,436 B2 | 4/2012 | Cheung |
| 8,282,925 B2 | 10/2012 | Tessier et al. |
| 8,481,270 B2 | 7/2013 | Gniewek et al. |
| 8,703,417 B2 | 4/2014 | Bieniarz et al. |
| 9,597,676 B2 | 3/2017 | Liu et al. |
| 10,059,978 B2 | 8/2018 | Akkus et al. |
| 10,151,035 B2 | 12/2018 | Naab |
| 10,359,421 B2 | 7/2019 | Shimada et al. |
| 11,408,854 B2 | 8/2022 | Baig et al. |

(Continued)

FOREIGN PATENT DOCUMENTS

| | | |
|---|---|---|
| CN | 106404758 A | 2/2017 |
| CN | 108531628 A | 9/2018 |
| CN | 106868479 B | 9/2019 |
| CN | 106568773 B | 2/2020 |
| CN | 111491625 A | 8/2020 |
| CN | 114767848 A | 7/2022 |
| CN | 115201175 A | 10/2022 |
| EP | 0 063 005 B1 | 10/1982 |
| EP | 0 126 617 A2 | 11/1984 |

(Continued)

OTHER PUBLICATIONS

Ahern, H. The Scientist 9(15) :20 (Year: 1995).*

(Continued)

*Primary Examiner* — Ethan C Whisenant

(74) *Attorney, Agent, or Firm* — Scully, Scott, Murphy & Presser, P.C.

(57) ABSTRACT

The present disclosure is directed to a kit and methods for using the same. The kit includes a plate including at least one well, wherein the well includes a silver nitrate and a catalyst. The method includes providing a sample of synovial fluid to a well of a plate, wherein the well includes a silver nitrate and a catalyst and determining a presence of monosodium urate (MSU) crystals, wherein the presence of MSU crystals indicates that gout is detected in the sample.

17 Claims, 8 Drawing Sheets
(8 of 8 Drawing Sheet(s) Filed in Color)

(56)         References Cited

U.S. PATENT DOCUMENTS

| | | | |
|---|---|---|---|
| 11,740,233 B2 | 8/2023 | Ashworth-Sharpe et al. | |
| 11,815,463 B1 | 11/2023 | Holmes et al. | |
| 12,097,247 B2 | 9/2024 | Pyun | |
| 12,135,325 B2 | 11/2024 | Nitz et al. | |
| 2006/0286684 A1 | 12/2006 | Brennan et al. | |
| 2007/0161559 A1 | 7/2007 | Petrilli et al. | |
| 2008/0062369 A1 | 3/2008 | Song et al. | |
| 2008/0213783 A1 | 9/2008 | Hainfeld | |
| 2008/0286803 A1* | 11/2008 | Verheijen | G01N 33/564 |
| | | | 435/7.1 |
| 2009/0029480 A1 | 1/2009 | Loane | |
| 2011/0020170 A1 | 1/2011 | Luinstra et al. | |
| 2011/0068734 A1* | 3/2011 | Waldron | H01M 10/4285 |
| | | | 320/107 |
| 2012/0283141 A1 | 11/2012 | Bieniarz et al. | |
| 2013/0059868 A1 | 3/2013 | Miner et al. | |
| 2013/0260400 A1* | 10/2013 | Jensen | G01N 33/6878 |
| | | | 435/7.92 |
| 2014/0329300 A1* | 11/2014 | Lundt | C12M 41/36 |
| | | | 435/287.2 |
| 2015/0017258 A1 | 1/2015 | Azzazy et al. | |
| 2016/0310063 A1 | 10/2016 | Curran et al. | |
| 2017/0143829 A1 | 5/2017 | Aslan | |
| 2017/0329120 A1* | 11/2017 | Hsu | G02B 21/0008 |
| 2018/0363024 A1 | 12/2018 | Akkus et al. | |
| 2019/0064113 A1 | 2/2019 | Baig et al. | |
| 2020/0062871 A1* | 2/2020 | Johnson | C08F 2/38 |
| 2021/0338774 A1 | 11/2021 | Jay et al. | |

FOREIGN PATENT DOCUMENTS

| | | | |
|---|---|---|---|
| EP | 0 481 020 B1 | 4/1992 | |
| EP | 1 249 730 B1 | 10/2002 | |
| EP | 1 597 578 B1 | 11/2005 | |
| EP | 1 642 131 B1 | 4/2006 | |
| EP | 1967885 A1 * | 9/2008 | G01N 21/6458 |
| EP | 3 270 928 B1 | 1/2018 | |
| EP | 3 782 603 A1 | 2/2021 | |
| EP | 3 805 760 A1 | 4/2021 | |
| GB | 1 282 089 | 7/1972 | |
| JP | 4800195 B2 | 8/2006 | |
| JP | 2009-85700 A | 4/2009 | |
| JP | 4648902 B2 | 3/2011 | |
| JP | 2014-57944 A | 4/2014 | |
| JP | 6322690 B2 | 6/2017 | |
| JP | 2020-187103 A | 11/2020 | |
| KR | 10-2091166 B1 | 3/2020 | |
| KR | 10-2125169 B1 | 6/2020 | |
| KR | 10-2148602 B1 | 8/2020 | |
| KR | 10-2250446 B1 | 5/2021 | |
| KR | 10-2021-0117534 A | 9/2021 | |
| KR | 10-2022-0071512 A | 5/2022 | |
| TW | I454696 B | 10/2014 | |
| WO | 91/03718 A1 | 3/1991 | |
| WO | 2004/086044 A1 | 10/2004 | |
| WO | WO 2004/099784 A2 | 11/2004 | |
| WO | 2008/109617 A1 | 9/2008 | |
| WO | WO-2010138539 A2 * | 12/2010 | A61K 31/5415 |
| WO | 2011/103439 A1 | 8/2011 | |
| WO | 2015/089644 A1 | 6/2015 | |
| WO | 2016/119570 A1 | 4/2016 | |
| WO | 2017/205530 A1 | 11/2017 | |
| WO | 2021/087116 A1 | 5/2021 | |
| WO | 2021/257554 A1 | 12/2021 | |

OTHER PUBLICATIONS

Barron, ESG. J.of Experimental Medicine52(3):447-456 (Year: 1930).*

Dovrou et al., PNAS 119(6) : e2113265119 (Year: 2022).*

Kaur et al., Colloids and Surfaces B:Biointerfaces 111 : 97-106 (Year: 2013).*

Wei Li et al., Biomaterial 65: 93-102 (Year: 2015).*

Stana et al., Bimacromolecules 18: 2732-2746 (Year: 2017).*

Tixier et al. J. Genet. & Breed. 51: 175 (Year: 1997).*

Barron EA The Catalytic Effect of Methylene Blue on the oxygen consumption of tumors and normal tissues. J. Exp. Med. 52(3) :447 (Year: 1930).*

Bartley, EH. The rapid estimation of uric acid in urine. JACS 19(8) :649 (Year: 1897).*

Folin et al. A new colorimetric method for the determination of uric acid in blood. JBC13(4) :469 (Year: 1913).*

Hainer et al., Diagnosis, treatment and prevention of gout. American Family Physician 90 (12) :831 (Year: 2014).*

Halverson et al., Identification of hydroxyapatite crystals in synovial fluid. Arthritis and Rheumatism 22(4) : 389 (Year: 1979).*

Lazcano et al., Clinical Utility of the Alizarin Red S stain on permanent preparations to detect calcium containing compounds in synovial fluid. Am. J. Clinical Pathol. 99:90-96 (Year: 1993).*

McCarty et al. Identification of urate crystals in gouty synovial fluid . Ann Inter. Med 54:452-460 (Year: 1961).*

McCarty et al. The significance of calcium phosphate crystals in the synovial fluid of arthritic patients : the pseudogout syndrome. I. Clinical Aspects Ann Inter. Med 56:711-737 (Year: 1962).*

McGee-RusselSM. Histochemical Methods for Calcium. J. Histochem. Cytochem. 6:22-41 (Year: 1958).*

Ndiaye et al. Short Report :A Non-Radioactive DAPI-based High-Throughput In Vitro Assay to Assess Plasmodium falciparum Responsiveness to Antimalarials—Increased Sensitivity of P. falciparum to Chloroquine in Senegal. Am J. Trop Med. Hyg. 82(2) : 228 (Year: 2010).*

Paul et al., Alizarin Red S Staining as a screening test to fetect calcium compounds in synovial fluid. Arthritis and Rheumatism 26(2):191 (Year: 1983).*

Sours et al., Dyeing uric acid crystals with methylene blue. JACS 124:8630 (Year: 2002).*

Yamakawa et al. The utility of Alizarin Red S staining in Calcium Pyrophosphate Dihydrate Crystal Deposition Disease. The J. of Rheumatology 30(5) :1032 (Year: 2003).*

Bemenderfer (Tips and Techniques for Processing and Sectioning Undecalcified Murine Bone Specimens; (Matthew J. Hilton (ed.), Skeletal Development and Repair: Methods and Protocols, Methods in Molecular Biology, vol. 1130, DOI 10.1007/978-1-62703-989 -5_10, @ Springer Science+Business Media, LLC 2014).*

Amjadi (Microchim Acta (2012) 178:373-379).*

Boumans (Clin Rheumatol (2017) 36:1599-1605).*

Selvi E. et al., "Diff Quick Staining Method for Detection and Identification of Monosodium Urate and Calcium Pyrophosphate Crystals in Synovial Fluids", Ann Rheum Dis 60:194-198 (2001).

Wu D. et al., "Uricase-Stimulated Etching of Silver Nanoprisms for Highly Selective and Sensitive Colorimetric Detection of Uric Acid in Human Serum", Sensors and Actuators B 221:1433-1440 (2015).

International Search Report dated Aug. 24, 2018 issued in PCT/US2018/032220.

Li, R. et al., "Synergistic Reaction of Silver Nitrate, Silver Nanoparticles, and Methylene Blue Against Bacteria", PNAS (Nov. 29, 2016), vol. 113, No. 48, pp. 13612-13617.

Zamudio-Cuevas, Y. et al., "Monosodium Urate Crystals Induce Oxidative Stress in Human Synoviocytes", Arthritis Research & Therapy (2016), vol. 18, No. 117, DOI:10.1186/s13075-016-1012-3, pp. 1-9.

Zhang, Y. et al., "Wide-Field Imaging of Birefringement Synovial Fluid Crystals Using Lens-Free Polarized Microscopy for Gout Diagnosis", Scientific Reports (Jun. 30, 2016), vol. 6:28793, DOI:10.1038/srep28793, pp. 3-14.

Faryna, A. et al., Chapter 166, Joint Fluid. Clinical Methods: The History, Physical, and Laboratory Examinations, 3rd Edition. Butterworths. Boston, 1990; pp. 773-776.

Boumans, D. et al., The Added Value of Synovial Fluid Cenliifugation for Monosodium Urate and Calcium Pyrophosphate Crystal Detection. Clin Rheumatol. (Apr. 19, 2017), DOI:10.1007/s10067-017-3633-6 10.1007/s10067-017-3633-6.

"Gout Disease Directly Detected by GoutiFind™, New Non-Invasive Diagnostic Test from Boulder Diagnostics", Boulder Diagnostics (Oct. 18, 2013).

(56) References Cited

OTHER PUBLICATIONS

"Novel Diagnostic Strip for Gout Patients Using a Single Teardrop", The Korea Advanced Institute of Science and Technology (KAIST) (May 3, 2017).

Gordon C. et al., "Detection of Crystals in Synovial Fluids by Light Microscopy: Sensitivity and Reliability", Annals of the Rheumatic Diseases 48:737-742 (1989).

Shidham V. et al., "Staining Method to Demonstrate Urate Crystals in Formalin-Fixed, Paraffin-Embedded Tissue Sections", State of the Art in Clinical and Anatomic Pathology 124:774-776 (May 2000).

Shoji K., "Alizarin Red S Staining of Calcium Compound Crystals in Synovial Fluid", Nihon Seikeigeka Gakkai Zasshi 67(4):201-210 (Apr. 1993), Abstract only.

Yavorskyy A. et al., "Detection of Calcium Phosphate Crystals in the Joint Fluid of Patients With Osteoarthritis-Analytical Approaches and Challenges", Analyst 133:302-318 (2008).

* cited by examiner

Uric acid crystals

METHOD AND KIT FOR DETERMINING THE PRESENCE OF MONOSODIUM URATE CRYSTALS IN JOINT SYNOVIAL FLUID

CROSS-REFERENCE TO RELATED APPLICATIONS

The present application claims benefit of U.S. Provisional Applications 62/504,623 filed on May 11, 2017, the contents of both of which are incorporated by reference.

BACKGROUND OF THE DISCLOSURE

Gout is a form of arthritis that develops in some people who have high levels of uric acid in the blood. Uric acid can form needle-like crystals in joints and cause sudden, severe episodes of pain, tenderness, redness, warmth and swelling in joints. Pain and inflammation occur when too much uric acid crystallizes and deposits in the joints as monosodium urate crystals MSU).

Gout has become more common in the United States in the past two decades, in part because of the nation's obesity crisis and a greater frequency of high blood pressure, new research indicates. Gout, a type of arthritis that occurs when uric acid crystals build up in the joints, was also found to be more common in men than in women. The condition now affects about 8.3 million people, or about 4% of the population. And the risk of getting gout increases with age. Gout, an inflammatory arthritis triggered by crystallization of uric acid inside the joints, causes swelling and severe pain. Gout can cause an attack of sudden burning pain, stiffness, and swelling in a joint, usually a big toe. These attacks can happen over and over unless gout is treated. Over time, they can harm joints, tendons, and other tissues.

To diagnose gout, physicians typically will take a patient's medical history, examine the affected joint and perform a blood test. A blood test to measure the level of uric acid in the blood is the typical first step to diagnose gout. However, a high level of uric acid in the blood doesn't necessarily mean that the patient has gout, just as a normal level doesn't mean that the patient does not have gout. The physician also has to rule out other potential causes of joint pain and inflammation such as infection, injury or another type of arthritis. An X-ray, ultrasound, CT or MRI to examine soft tissue and bone are also typically performed to diagnose and confirm gout.

Identifying monosodium urate crystals in joint fluid is a typical way to diagnose gout. Injecting a needle into the joint and removing synovial fluid from the affected joint and examining it under a microscope for uric acid crystals is typically done for gout diagnosis.

Also, gout is caused by uric acid crystals, pseudo gout is caused by calcium pyrophosphate crystals (CPP) and CPP are often found in joint fluids along with MSU. Both these types of crystals cannot be detected and distinguished by the naked eye. Hence, a complex technique like polarized microscopy is utilized in clinical labs to distinguish and identify MSU. This technique is expensive, time consuming and also requires trained technicians to accurately identify and report gout.

Thus, what is desired is a relatively quick method and device to detect and/or diagnose gout from a sample taken from a patient.

Embodiments of the present disclosure provide devices and methods that address the above clinical needs.

SUMMARY OF THE DISCLOSURE

The present disclosure is directed to a kit and methods for using the same. The kit comprises a plate comprising at least one well, wherein the well comprises a silver nitrate and a catalyst. The method comprises providing a sample of synovial fluid to a well of a plate, wherein the well comprises a silver nitrate and a catalyst and determining a presence of monosodium urate (MSU) crystals, wherein the presence of MSU crystals indicates that gout is detected in the sample.

BRIEF DESCRIPTION OF THE DRAWINGS

The present disclosure will be better understood by reference to the following drawings, which are provided as illustrative of certain embodiments of the subject application, and not meant to limit the scope of the present disclosure.

The patent or application file contains at least one drawing executed in color. Copies of this paper or patent application publication with color drawing(s) will be provided by the Office upon request and payment of the necessary fee.

DETAILED DESCRIPTION OF THE DISCLOSURE

Figure 1:
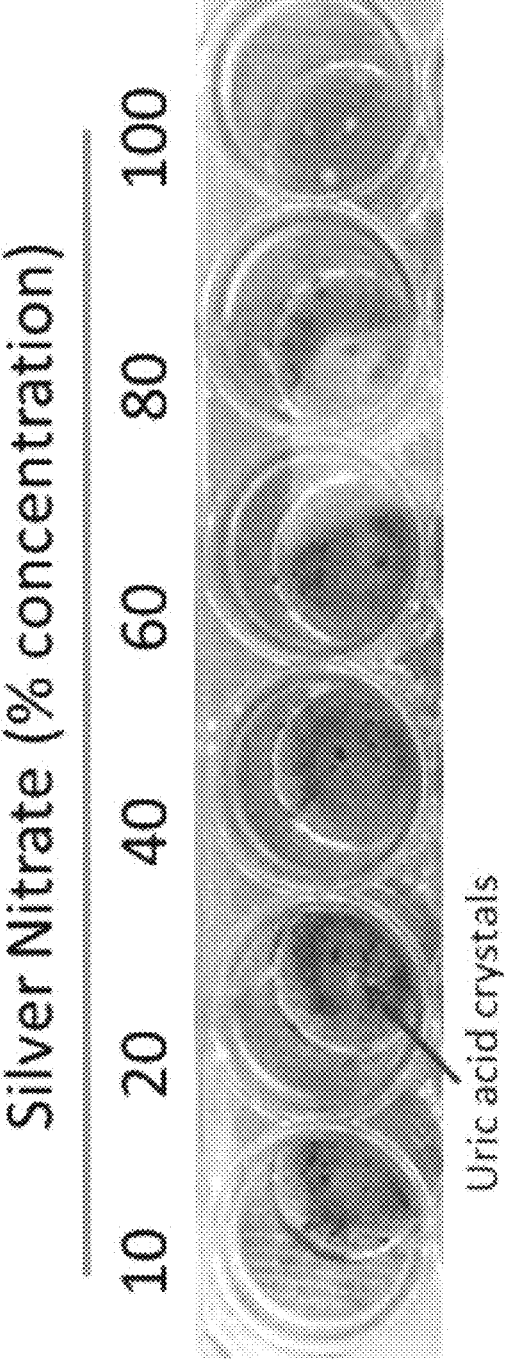
FIG. 1 is an image of various concentrations of silver nitrate solution.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one embodiment", "certain embodiments", some embodiments" or "an embodiment", indicate that the embodiment(s) described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, is present on second element, wherein intervening elements interface between the first element and the second element. The term "direct contact" or "attached to" means that a first element, and a second element, are connected without any intermediary element at the interface of the two elements.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

The present disclosure includes a kit that includes a plate having at least one well, wherein the well comprises any suitable ionic silver compound, such as silver nitrate and a catalyst. This kit is configured to detect gout in a sample, such as a synovial fluid sample that has been collected from a patient. This synovial fluid sample can be collected in any suitable way, such as by a hypodermic needle.

The catalyst can be any suitable catalyst, such as formaldehyde, citric acid, glutaraldehyde, and combinations thereof. The catalyst can be in any suitable concentration, such as from about 0.001% to about 4%, or about 0.002% to about 2%, or about 0.003% to about 1%, or about 0.01% to about 0.5%, and all ranges therein. Along with the catalyst, a basic material, such as sodium bicarbonate, can also be included.

The plate of the kit can be any suitable surface and can be comprised of any suitable material, such as glass, plastic, and combinations thereof. The well includes vertical walls that rise above the surface of the plate or are sunken below the surface of the plate. The well care be any suitable shape or size and is configured to maintain a fluid within it.

Within the well, the kit includes an ionic silver compound, such as silver nitrate, at any suitable concentration, such as about 10% to about 40%, or about 20%. As an example, 20% silver nitrate solution is about 1.34 M $AgNO_3$. Also within the well, a suitable catalyst is included. In one embodiment, the catalyst is formaldehyde, which can be at any suitable concentration, such as a concentration of about 0.002%.

Within the well the ionic silver compound, such as silver nitrate, and the catalyst can be elements of a solution that is maintained in the well, and/or, the ionic silver compound, such as silver nitrate, and the catalyst can be elements of a film that at least partially coats an internal surface of the well. The coating on the internal surface of the well can occur on a portion of or the whole bottom surface, in addition to or in replace of a portion of or the whole side wall surface of the well.

If the ionic silver compound, such as silver nitrate, and the catalyst are elements of a solution, the synovial fluid sample can be added to the solution within the well and the mixture can react.

If the ionic silver compound, such as silver nitrate, and the catalyst are elements of a film that at least partially coats an internal surface of the well, the synovial fluid sample can be added to the well to react with the film.

Optionally, as an additional component of the kit, within the well, the well can further comprise any suitable calcium detecting stain, such as alizarin red, Von Kossa stain, and combinations thereof, which can be in any suitable concentration, such as about 0.01% to about 3%, or about 0.5% or about 2%, or about 0.8% to about 1.5%, or about 2% solution of calcium detecting stain.

Optionally, as an additional component of the kit, within the well, the well can further comprise a polymerizing matrix material, such as a gelatin, an agar and combinations thereof. This polymerizing matrix material may be included in the well as an element to contact the solution of ionic silver compound and catalyst, or, the polymerizing matrix material may be included in the well as an element of the film of ionic silver compound and catalyst.

In the well, if uric acid is present in the synovial fluid sample, it reacts with the ionic silver compound, such as silver nitrate, and forms a dark or darkish color crystal, such as a monosodium urate (MSU) crystal. To aid in viewing of the MSU crystal, the kit can include and can be configured to attach to a camera to image the contents of the well after a reaction. This camera can be any suitable camera device that is capable of capturing an image, and the attachment between the camera and kit can be any suitable structural arrangement that can maintain or substantially maintain the camera's location as compared to the well.

Optionally, the camera can include a magnification system, such as one or more magnifying lenses.

In another embodiment, the kit can include a hinged cover that substantially covers an upper opening of the well. The hinged cover can include a cover bottom, which extends around an upper surface of the well, as well as a cover top. The cover top can include a magnifier, so that when the cover top is in a closed configuration, the magnifier magnifies the contents of the well.

The methods of the present disclosure can be used in conjunction with the above described kit. Methods of the present disclosure include methods of detecting gout by providing a sample of synovial fluid to the well of the plate, which comprises an ionic silver compound, such as silver nitrate, and the catalyst. The synovial fluid can be collected from any patient in any suitable way, such as by a hypodermic needle being inserted into a joint, and the fluid therein being withdrawn into the hypodermic needle. The hypodermic needle can then be used to transport the fluid and then provide the fluid into the well.

The method then includes the determination of the presence of monosodium urate (MSU) crystals, wherein the presence of MSU crystals indicates that gout is detected in the sample. If uric acid was present in the synovial fluid, an amount of MSU crystal should be formed in the well. The MSU crystal will be dark or darkish in color as compared to the remaining fluid within the well and can be visible by the naked eye, through a magnifier or through an image (magnified or not) of the contents of the well.

The amount of time between providing the synovial fluid to the well and determining whether or not MSU crystal are present can be about 3 minutes or more, about 5 minutes or more, about 8 minutes or more, about 10 minutes or more, about 15 minutes or more, about 20 minutes or more, or more than 20 minutes.

The methods and model of the present disclosure will be better understood by reference to the following Examples, which are provided as exemplary of the disclosure and not in any way limiting.

EXAMPLES

Interaction of Uric Acid Crystals with Silver Nitrate

Uric acid interacts with silver nitrate s black after reducing the silver. This chemical reaction is used as the basis for detecting monosodium urate (MSU) crystals. MSU crystals were placed in glass wells of a 24-well cell culture plate and 200 µL of different concentrations of silver nitrate solution (100%, 80%, 60%, 40%, 20% and 10%) with 0.002% formaldehyde was added to each of the wells.

The culture plate was allowed to incubate at room temperature and the image of FIG. 1 was acquired. As can be seen in FIG. 1, from left to right, the concentrations of silver nitrate solution increases as indicated by the numbers above each well, from 10% to 100%. Also as can be seen in FIG. 1, 20% silver nitrate solution included maximum staining as compared to the other concentrations of silver nitrate solution.

Gout Detection Device with Pre-Coated Staining Agent

Figure 2:
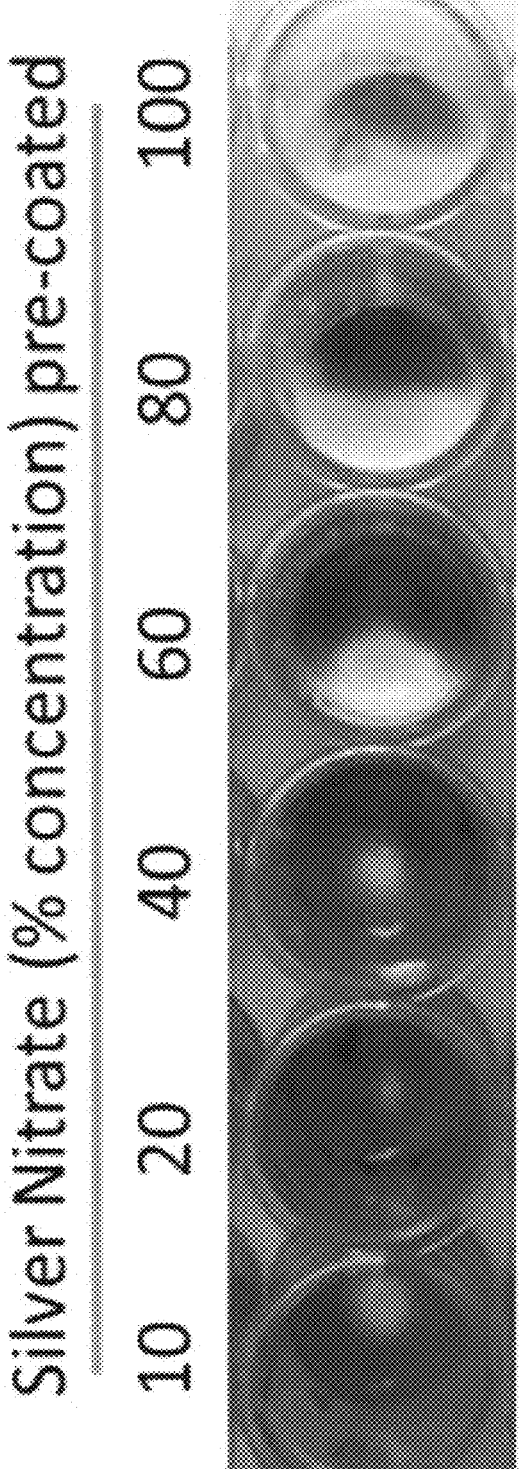
FIG. 2 is an image of various concentrations of silver nitrate films.

Different concentrations of silver nitrate with 0.002% formaldehyde solution were added to different wells of a well culture plate and allowed to air dry overnight. MSU crystal (1 mg/200 µL) suspension was prepared in saline and added to the wells containing the dried silver nitrate/formaldehyde film that coated inner portions of the well. FIG. 2 is an image that was acquired after addition of the suspension to the wells.

As can be seen in FIG. 2, from left to right, the concentrations of silver nitrate in the films is indicated by the numbers above each well, from 10% to 100%. Also as can be seen in FIG. 2, 20% silver nitrate solution included maximum staining as compared to the other concentrations of silver nitrate solution.

Distinguishing Uric Acid Crystals from Calcium Crystals

Calcium phosphate crystals are often found to be present in joint fluids and is an indication of pseudo gout. To distinguish uric acid crystals from calcium phosphate crystals, alizarin red (2%) solution was tested on MSU crystals (also referred to herein as uric acid crystals). Silver nitrate solution turns MSU crystals black, whereas alizarin red does not interact with the MSU crystals.

In this example, alizarin red does not substantially interact with MSU crystals as the crystals remain white even after exposure of MSU crystals to alizarin red stain.

Figure 3:
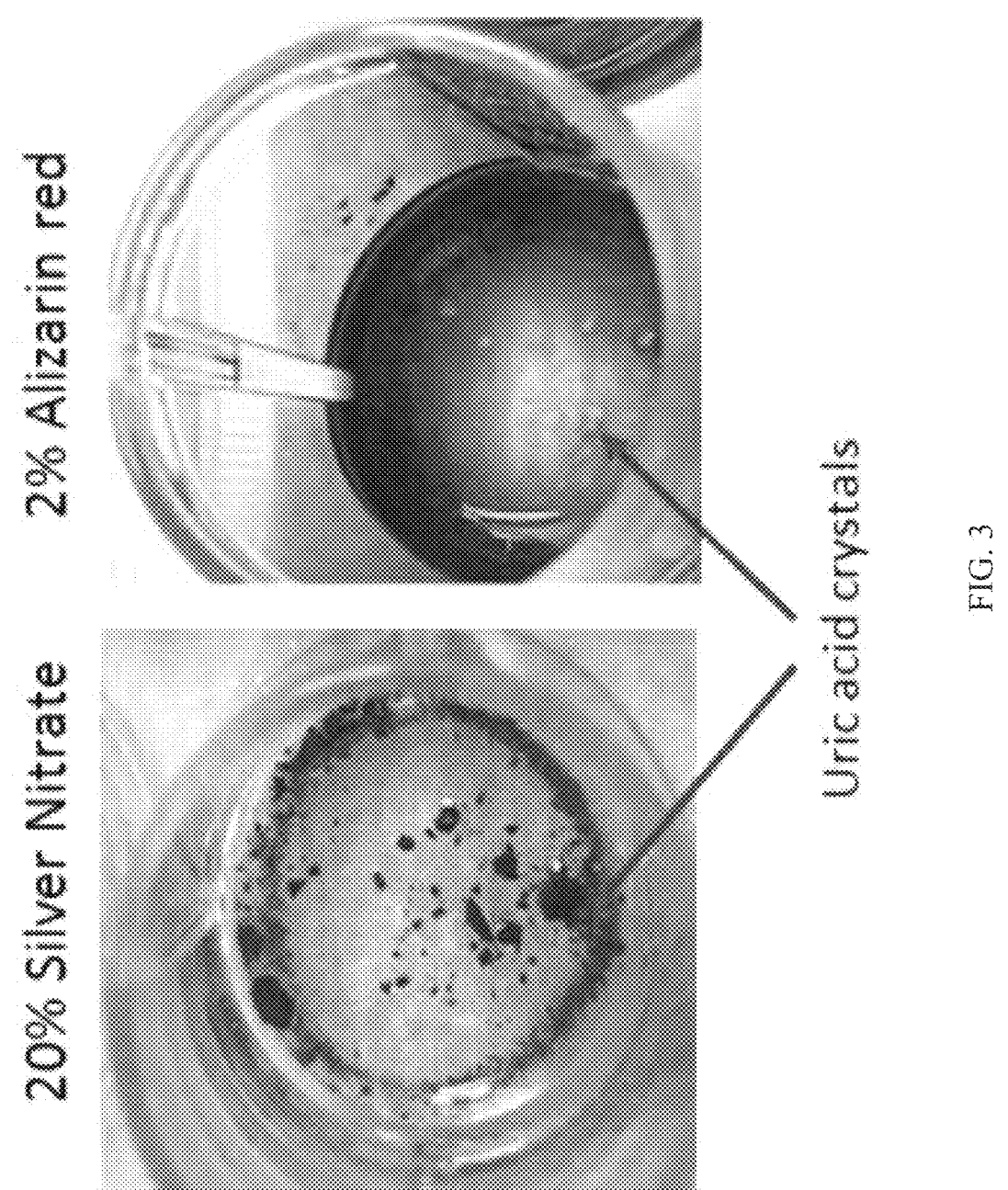
FIG. 3 is an image of monosodium urate (MSU) crystals in a silver nitrate solution and also in a 2% Alizarin red solution.

FIG. 3 is an image of a side by side comparison of MSU crystals in a silver nitrate solution and also in a 2% Alizarin red solution. On the left, the MSU crystals have interacted with the silver nitrate and are now seen as being black in color. On the right, the MSU crystals in the Alizarin red solution are not black since calcium phosphate (calcium) interacts with Alizarin red and give a deep orange to red color rather than black.

Gout Detection Kit

Figures 4A, 4B:
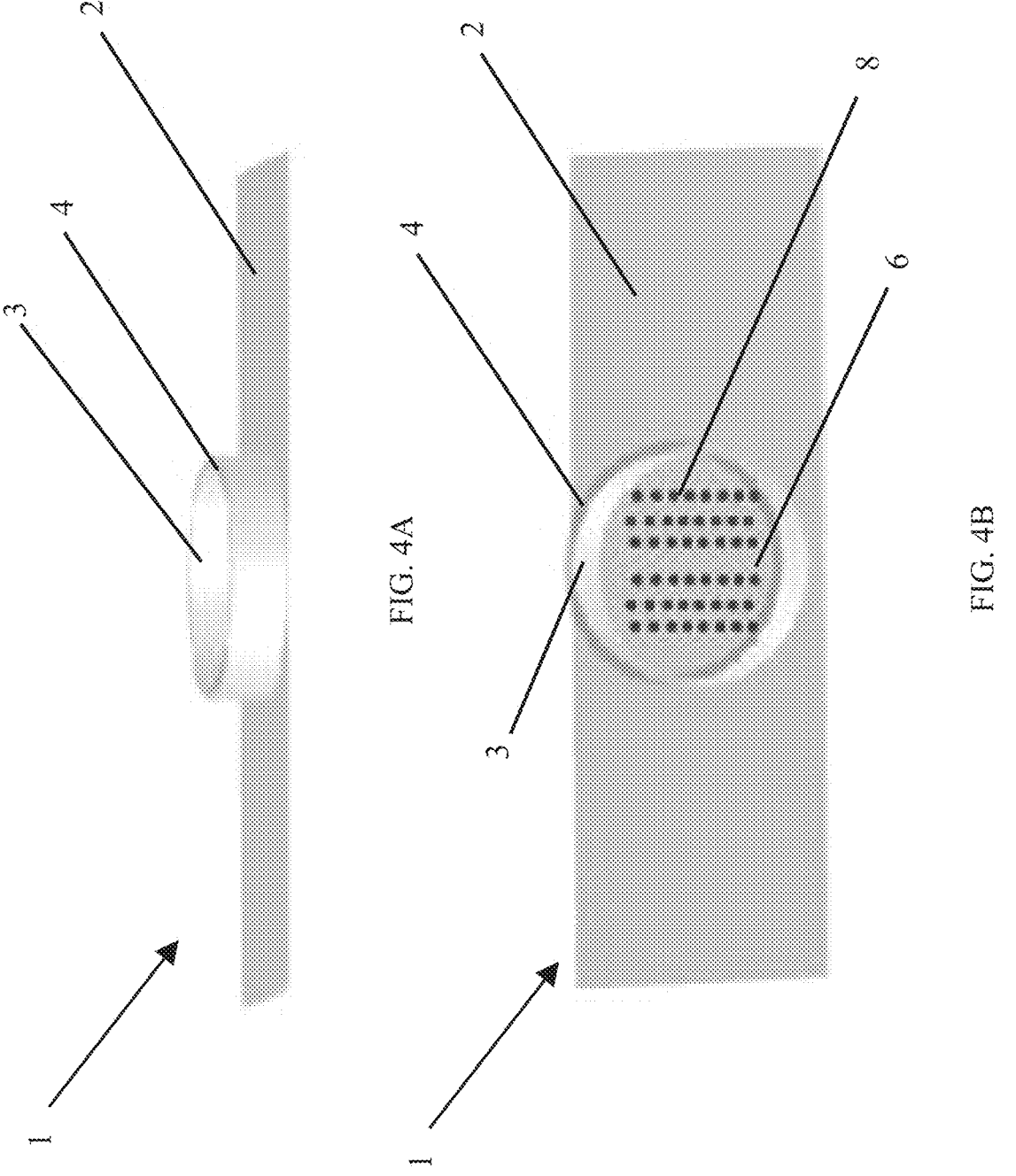
FIGS. 4A and 4B are illustrations of a kit configured to detect gout.

To identify MSU crystals in synovial fluid aspirated from a joint, one embodiment of a kit 1 configured to detect gout was designed one embodiment of which is shown in FIG. 4A. FIG. 4A is a side view of the kit 1. The kit 1 of FIG. 4A includes a plate 2 that comprises a well 4. In this embodiment only one well is shown, but, in other embodiments, two or more its may be present on the plate 2. An inner side surface 3 of the well 4 can be seen in FIG. 4A.

FIG. 4B is a perspective view of the kit 1. As can be seen in FIG. 4B, the well 4 is substantially round, and in this embodiment has a diameter of 1:5 mm, but, in other embodiments, the well can be different shapes and/or larger or smaller diameters. Well 4 can be formed of any suitable material, such as plastic, glass, metal, carbon materials, and mixtures thereof. In this embodiment plate 2 is formed of a glass material, but, plate 2 can be formed of any suitable material, such as plastic, glass, metal, carbon materials, and mixtures thereof.

In the embodiment of FIG. 4B, a base surface 6 of the well 4 is coated with 20% silver nitrate with 0.002% formaldehyde to form a coating 8. Coating 8 is formed in any suitable way, in this embodiment by overnight incubation and air drying of the silver nitrate and formaldehyde in the well 4. Although coating 8 is shown as discrete dots in FIG. 4, this coating 8 did extend over the base surface 6 of the well 4. Joint fluid (about 200 uL, but can be less or more) can be added to the well 4 for detection of MSU crystals.

Gout Detection Kit

Figure 5:
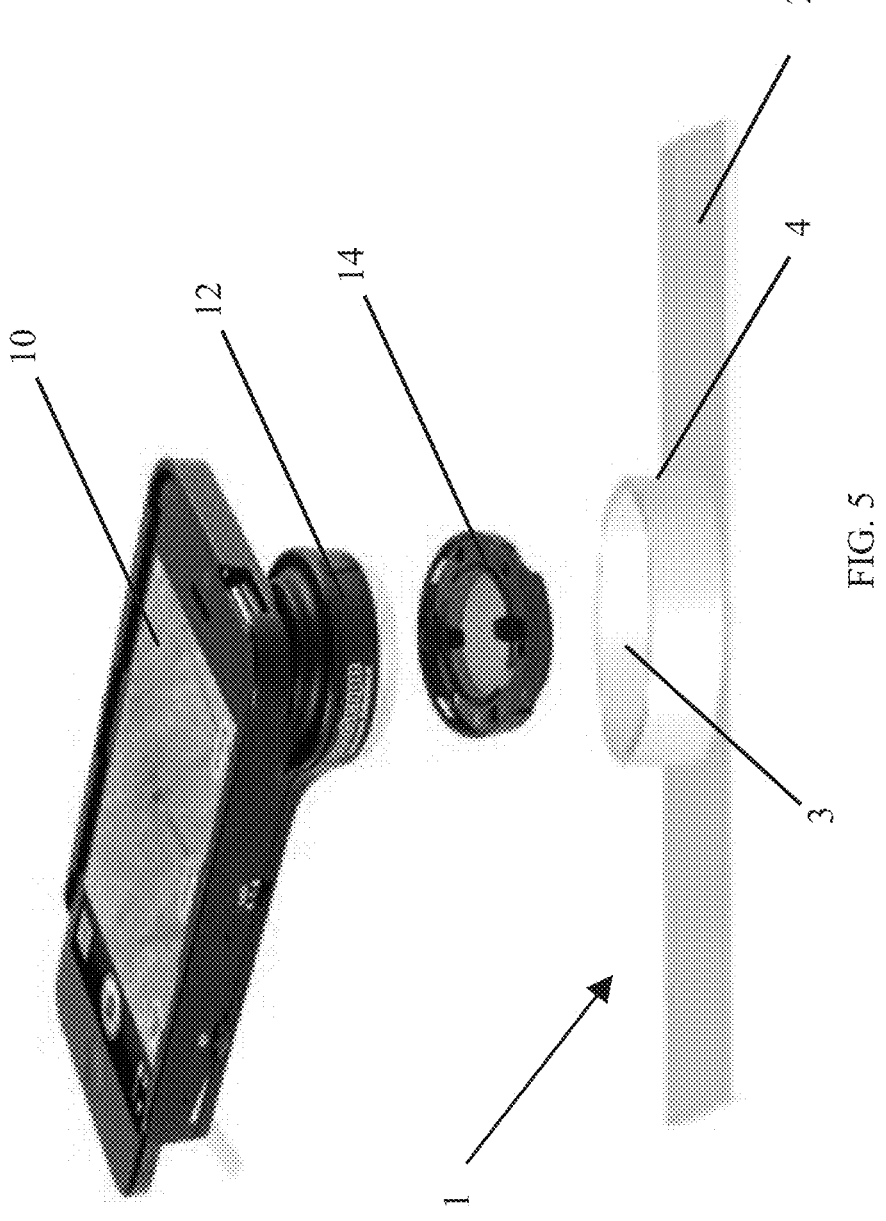
FIG. 5 is an illustration of a kit configured to detect gout.

FIG. 5 illustrates an embodiment of kit 1, which includes a camera device 10 (in this example an iPhone® 6, but in other embodiments can be any apparatus capable of capturing images), an optional magnification system 12 (in this embodiment a Micromobile microscope (Proscope™) but in other embodiments, any suitable lens or lenses configured to magnify an image) and an optional filter 14 (in this embodiment a polarizing filter, but in other embodiments, any one or more suitable filters can be included)

In the kit of FIG. 5, MSU crystals suspension and calcium phosphate solution were added to the well 3. In this embodiment, the well 3 was pre-coated with 20% silver nitrate, 0.002% formaldehyde and 2% alizarin red. After 5 minutes, low magnification (10×) and high magnification (100×) images were acquired with the camera device 10 of the contents of the well 5, and are shown in FIGS. 6A and 6B.

Figures 6A, 6B:
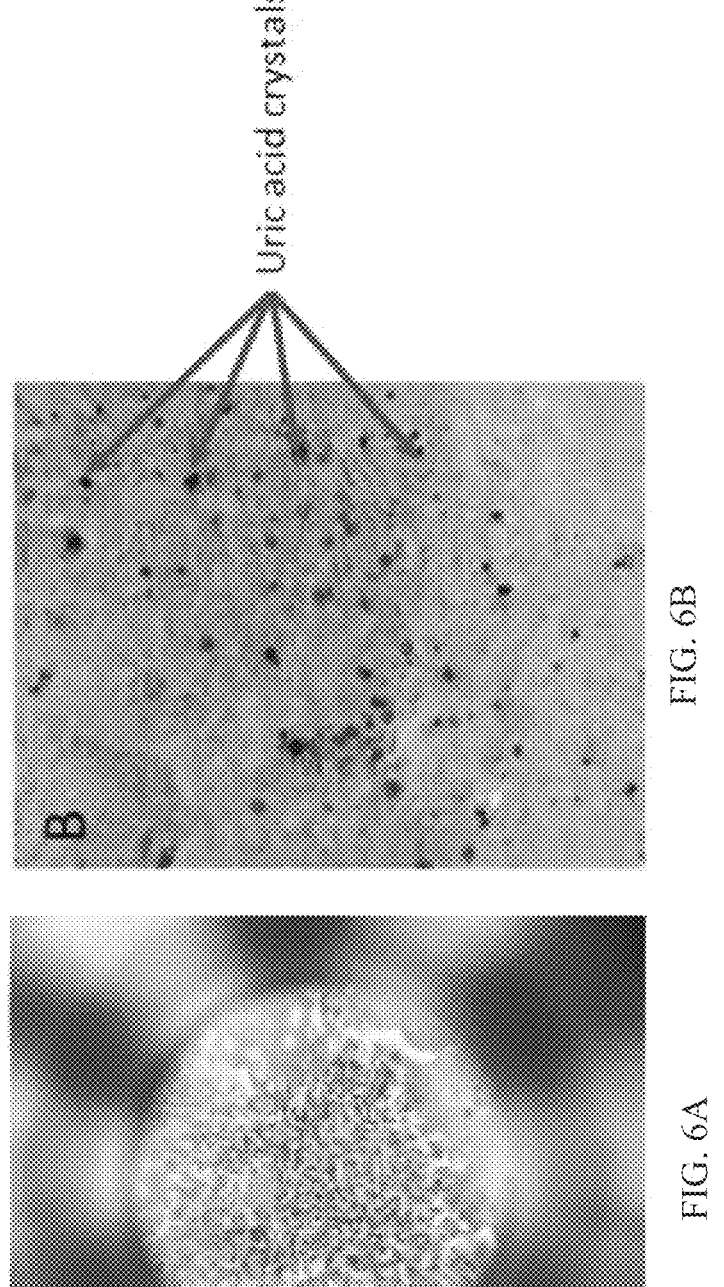
FIGS. 6A and 6B are magnified images of a sample within the kit of FIG. 5.

FIG. 6A is an image at a magnification of 10X, FIG. 6B is an image at a magnification of 100×. The images of both FIGS. 6A and 6B were acquired without the use of optional filter 14. As indicated in FIG. 6B, uric acid (MSU) crystals were formed, and are shown as being stained black.

Another embodiment of a kit 20 is shown in FIG. 7.

Figures 7A, 7B:
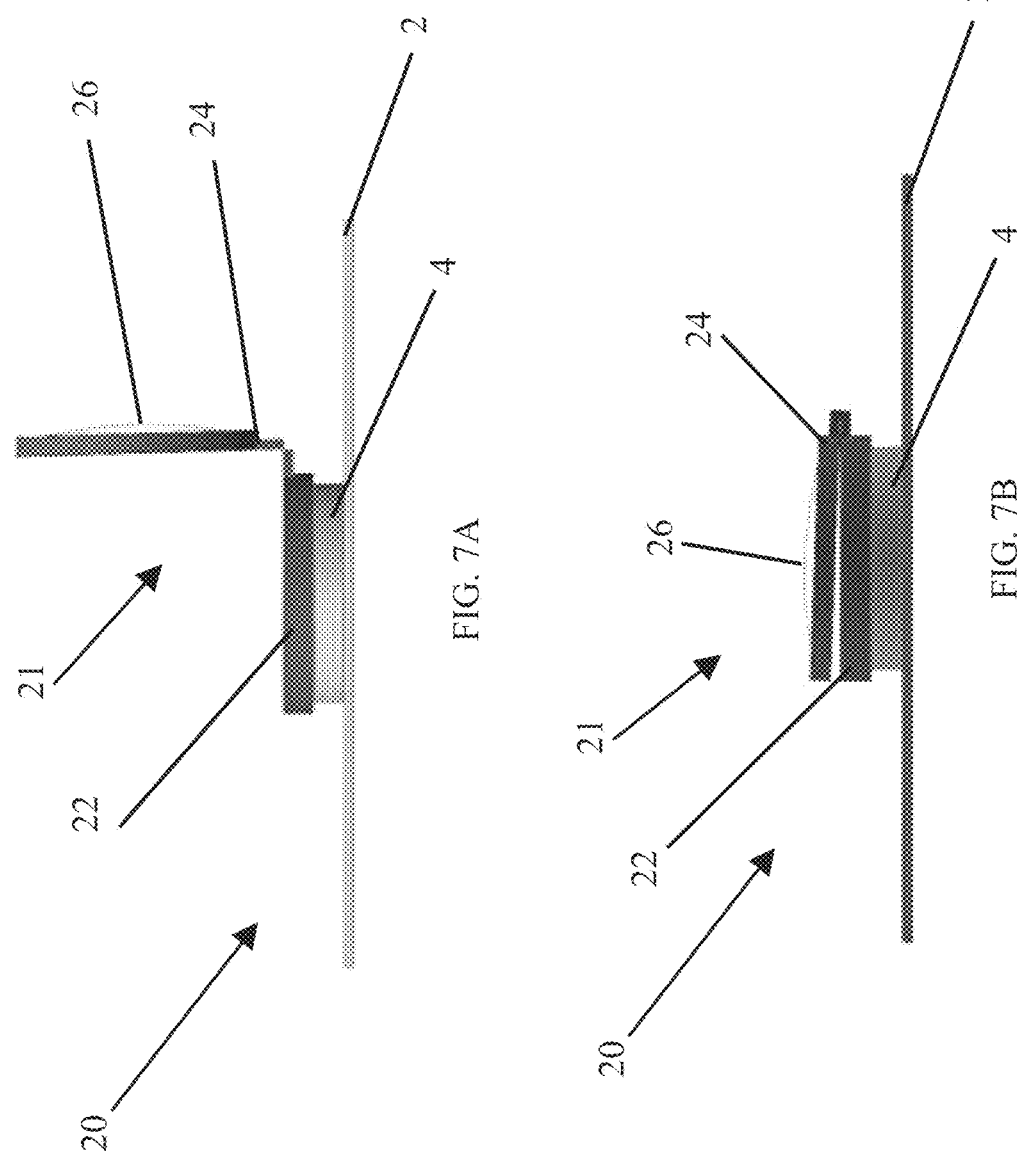
FIGS. 7A-7C are illustrations of a kit configured to detect gout.

Kit 20 includes the plate 2 and well 4, with the well 4 being covered with a hinged cover 21. The hinged cover 21 includes a cover base 22, that extends around the upper circumference of the well 4 and has an opening therethrough (better seen in FIG. 7C), and a cover top 24. In FIG. 7A, the hinged cover 21 is shown in an open configuration.

Figure 7C:
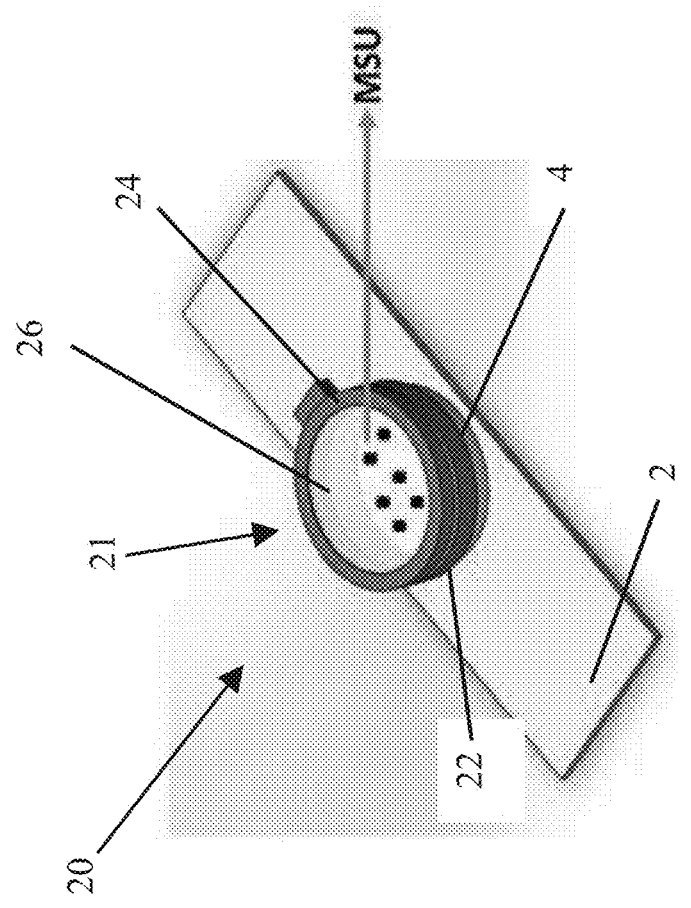

The cover top 24 includes a magnifier 26 (better seen in FIG. 7C) that is substantially transparent or substantially translucent and is configured to magnify the contents of well 4 for observation when the hinged cover 21 is in a closed configuration (as in seen in FIGS. 7B and 7C).

Magnifier 26 can be any suitable shape and any material suitable for magnifying the contents of well 4. Some examples of the material of magnifier 26 is plastics, glasses, and combinations thereof. The shape and material of magnifier 26 can be adjusted to result in a desired magnification value, such as for example a magnification of about 60×, but, in other embodiments, the magnification can be any value between about 2× and about 100× or more.

As seen in FIG. 7B, which is a side illustration of the kit 20, hinged cover 21 can be in a closed configuration so that cover top 24 contacts or nearly contacts cover base 22.

FIG. 7C is a perspective illustration of the kit 20, with the hinged cover 21 being in a closed configuration. For illustrative purposes, the magnifier 26 is providing sufficient magnification such that MSU crystals (black dots) are visible to a human operator in the well 4, as the operator looks into the well 4 through the magnifier 26.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

The invention claimed is:

1. A kit configured to detect gout in a sample obtained from a patient comprising:
   a plate comprising at least one well, wherein the well contains a silver nitrate, formaldehyde, and alizarin red.

2. The kit of claim 1, wherein the silver nitrate and formaldehyde are components of a solution within the at least one well.

3. The kit of claim 1, wherein the silver nitrate and formaldehyde are comprised in a film that at least partially coats a surface of the at least one well.

4. The kit of claim 1, wherein the silver nitrate is in a range of concentration of about 10% to about 40%.

5. The kit of claim 1, wherein the silver nitrate is at a concentration of about 20%.

6. The kit of claim 1, wherein the formaldehyde is at a concentration of about 0.002%.

7. The kit of claim 1, wherein the kit is configured to attach to a camera.

8. The kit of claim 7, wherein the camera comprises a magnification system.

9. The kit of claim 1, wherein the well further comprises a solution of about 2% alizarin red.

10. The kit of claim 1, wherein the kit further comprises a hinged cover.

11. The kit of claim 10, wherein the hinged cover comprises a cover top, wherein the cover top comprises a magnifier.

12. A method of detecting gout, the method comprising:
   providing a sample of synovial fluid to a well of a plate, wherein the well contains a silver nitrate and formaldehyde;
   determining a presence of monosodium urate (MSU) crystals, wherein the presence of MSU crystals indicates that gout is detected in the sample.

13. The method of claim 12, wherein the time between the providing step and the determining step is about 5 minutes.

14. The method of claim 12, wherein the silver nitrate and the formaldehyde are components of a solution within the well.

15. The method of claim 12, wherein the silver nitrate and the formaldehyde are comprised in a film that at least partially coats a surface of the well.

16. The method of claim 12, wherein the silver nitrate is at a concentration of about 20%.

17. The method of claim 12, wherein the formaldehyde is at a concentration of about 0.002%.

* * * * *